US010786432B2

(12) United States Patent
Jornitz et al.

(10) Patent No.: US 10,786,432 B2
(45) Date of Patent: Sep. 29, 2020

(54) USE OF A DEVICE AND A METHOD FOR PREPARING MIXTURES OF PHARMACEUTICAL SUBSTANCES

(71) Applicant: Sartorius Stedim Biotech GmbH, Goettingen (DE)

(72) Inventors: Maik Jornitz, Manorville, NY (US); Stefan Schlack, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 49 days.

(21) Appl. No.: 16/197,560

(22) Filed: Nov. 21, 2018

(65) Prior Publication Data
US 2019/0083358 A1     Mar. 21, 2019

Related U.S. Application Data

(60) Continuation-in-part of application No. 15/366,034, filed on Dec. 1, 2016, now abandoned, which is a
(Continued)

(30) Foreign Application Priority Data

Apr. 12, 2011 (DE) .................. 10 2011 016 767

(51) Int. Cl.
*A61J 1/20*     (2006.01)
*A61M 39/08*     (2006.01)
(Continued)

(52) U.S. Cl.
CPC .............. *A61J 1/2089* (2013.01); *A61J 3/002* (2013.01); *A61M 39/08* (2013.01);
(Continued)

(58) Field of Classification Search
CPC ....... B65B 3/003; A61J 1/2096; A61J 1/2079; A61J 3/002
See application file for complete search history.

(56) References Cited

U.S. PATENT DOCUMENTS 4,219,038 A    8/1980 Lubitzsch et al.
5,592,940 A    1/1997 Kampfe et al.
(Continued)

FOREIGN PATENT DOCUMENTS

DE    3040212    5/1981
DE    3333283    4/1985
(Continued)

OTHER PUBLICATIONS

International Search Report dated Jul. 5, 2012.
German Patent Appl. No. 10 2011 016 767.6—Office Action dated Mar. 4, 2015.

Primary Examiner — Timothy P. Kelly
(74) Attorney, Agent, or Firm — Gerald E. Hespos; Michael J. Porco; Matthew T. Hespos

(57) ABSTRACT

A method for the preparing mixtures of pharmaceutical or biopharmaceutical substances (11, 11'') includes arranging a preparation container (3, 3', 3'') already made up with ingredients in a receptacle (2) of a device (1, 1', 1'') feeding a fluid (10) from a storage container (4, 4'') into the preparation container (3, 3'') via a feed line (6), preparing the ingredients with the fluid (10, 10'') into a substance mixture (11, 11''), and removing the substance mixture (11, 11'') from the preparation container (3, 3', 3'') into a receiving container via a discharge line (12, 12', 12''). A device also is provided for carrying out the method.

10 Claims, 8 Drawing Sheets

Related U.S. Application Data division of application No. 14/044,435, filed on Oct. 2, 2013, now abandoned, which is a continuation-in-part of application No. PCT/EP2012/001170, filed on Mar. 16, 2012.

(51) Int. Cl.
*A61J 3/00* (2006.01)
*B65B 3/00* (2006.01)

(52) U.S. Cl.
CPC ... *A61J 2205/10* (2013.01); *A61M 2205/3576* (2013.01); *A61M 2205/36* (2013.01); *A61M 2205/50* (2013.01); *A61M 2205/60* (2013.01); *A61M 2205/6054* (2013.01); *A61M 2205/6072* (2013.01); *A61M 2205/7509* (2013.01); *A61M 2205/7518* (2013.01); *B65B 3/003* (2013.01)

(56) References Cited

U.S. PATENT DOCUMENTS

| | | |
|---|---|---|
| 5,609,572 A | 3/1997 | Long |
| 5,941,867 A | 8/1999 | Kao |
| 7,174,923 B2 | 2/2007 | Schorn |
| 2005/0277833 A1 | 12/2005 | Williams, Jr. |
| 2007/0125442 A1 | 6/2007 | Tribble et al. |

FOREIGN PATENT DOCUMENTS

| | | |
|---|---|---|
| DE | 697 20 981 | 8/2004 |
| DE | 602005005049 T2 | 3/2009 |
| EP | 1 382 321 | 1/2004 |
| WO | 2005118031 | 12/2005 |
| WO | 2010125329 | 11/2010 |

USE OF A DEVICE AND A METHOD FOR PREPARING MIXTURES OF PHARMACEUTICAL SUBSTANCES

CROSS REFERENCE TO RELATED APPLICATION

This application is a continuation-in-part of application Ser. No. 15/366,034, which is divisional of application Ser. No. 14/044,435, which is a continuation-in-part of PCT/EP2012/001170, and which in turn claims priority on DE 10 2011 016 767.6, filed Apr. 12, 2011, the disclosures of which are incorporated herein by reference.

BACKGROUND

1. Field of the Invention

The invention relates a method that includes arranging a preparation container already made up with ingredients in a receptacle of a device, feeding a fluid from a storage container into the preparation container via a feed line, preparing the ingredients with the fluid into a substance mixture, and removing the substance mixture from the preparation container into a receiving container via a discharge line. The invention also relates to a device that includes a preparation container with ingredients that can be arranged in a receptacle, a storage container with a fluid that can be fed in a monitored manner to the preparation container via a feed line, and a receiving container that communicates with the preparation container via a discharge line.

2. Description of the Related Art

In the pharmaceutical and biopharmaceutical sector, in particular in the preclinical or clinical sector, and also in research and development, it is often necessary to prepare small volumes of buffers and media. The buffers and media are often prepared as already made up in accordance with predetermined formulations, which require careful and relatively time-consuming handling by the specialist personnel. It is particularly important in this respect to prepare substance mixtures that are made to conform to the volumes, concentrations and components or media required by the final consumer.

For example, WO 2010/125329 A1 discloses a device and a method for the portioned preparation of beverages, in particular for the preparation or brewing of coffee. This device consists of a preparation container with ingredients, that is coffee powder, that can be arranged in a receptacle of the known device, a storage container with a fluid, that is water, which is fed in a monitored manner to the preparation container via a feed line. The water that is fed to the preparation container in a heated form brews the coffee powder mixture, which is fed as a prepared substance mixture, that is as coffee, to a receiving container, that is a coffee cup, via a discharge line.

The preparation container is in this case formed as a closed capsule or cartridge, which contains the substance mixture to be prepared.

There are, however, also known devices that use a so-called pad instead of a capsule or cartridge.

The object of the invention is to provide a device and a method with which the preparation of mixtures of pharmaceutical or biopharmaceutical substances can be made possible even with prescribed small or medium volumes, concentrations and media or components that are easily and reliably made to suit the final consumer.

SUMMARY OF THE INVENTION

This object is achieved by the use of a device for preparing mixtures of pharmaceutical or biopharmaceutical substances, comprising a preparation container with ingredients that can be arranged in a receptacle, a storage container with a fluid that can be fed in a monitored manner to the preparation container via a feed line, and a receiving container that communicates with the preparation container via a discharge line.

A storage container should also be understood as meaning a fluid preparation system and, if the fluid is water, also a water preparation system for analytically pure water, as sold for example by Sartorius AG of Gottingen under the name Arium®. Other systems that may be used here are those that produce water for injection purposes. Such systems could be designed for example in the form of multicolumn distillation or falling film evaporation.

It has not so far occurred to a person skilled in the art to consider devices and methods such as those known for the preparation of beverages, such as coffee for example, for the preparation of mixtures of pharmaceutical or biopharmaceutical substances, which must take place under high-purity, sterile conditions.

Adaptation of known devices known for the use or preparation of mixtures of pharmaceutical or biopharmaceutical substances makes it possible even under high-purity, sterile conditions to prepare mixtures of pharmaceutical or biopharmaceutical substances relatively quickly, reliably and easily from small to medium amounts or volumes, in prescribable concentrations and media or components, that are made to suit the final consumer. In principle, this device is also suitable for larger amounts or volumes.

The invention preferably involves the use of the device for the preparation of medicaments that are individual to a patient.

The device preferably has a sterile filter or a virus filter or a combination of a sterile filter and a virus filter in the feed line to the preparation container and/or in the discharge line. As a result, it is ensured that only sterile and/or virus-free fluid is fed to the preparation container and only sterile and/or virus-free prepared substance mixture is fed to the receiving container.

The preparation container may be formed as a cartridge or a capsule. A cartridge or capsule may in this case have both the feed line and the discharge line on one side. However, it is also possible to use a pad or membrane pad as the preparation container. If a membrane pad is used, the feed line and the discharge line are arranged on opposite sides of the pad.

It is also possible to feed ingredients individually to the preparation container in the device from a plurality of storage containers. In principle, it is also possible to arrange two or more preparation containers next to one another in a parallel arrangement or one behind the other in a series arrangement. The preparation containers may be connected to one another by way of hose connections, which are for example welded in a sterile manner.

The preparation container may have a mixing arrangement that facilitates the preparation process. The mixing arrangement may in this case also be formed by mixing nozzles. The preparation container or the receiving container may also be vibrated in a vibrating device for the creation of a mixing process.

The device for the preparation of mixtures of pharmaceutical or biopharmaceutical substances preferably comprises a preparation container with ingredients that can be arranged in a receptacle, a storage container with a fluid that can be fed in a monitored manner to the preparation container via a feed line, a receiving container that communicates with the preparation container via a discharge line, and a sterile or virus filter or a combination thereof that may be arranged upstream or downstream of the preparation container.

The preparation container may have the at least one sterile or virus filter or a combination thereof. This filter or combination of filters may be arranged at inlet and/or outlet opening(s), inside and/or outside the preparation container.

In this respect, the preparation container may also be formed as a pad, on or in which a sterile filter is arranged.

The preparation container and the receiving container may be connected to one another by way of a hose connection or may be connected to one another, for example by sterile welding. Thus, the preparation container could have on the output side and the receiving container (for example a bag) could have on the input side a respective welded hose, the free ends of which are welded to one another in a sterile manner in a welding unit.

A filter device may be on the receiving container there and may have a mixing nozzle that ends in the receiving container.

The receiving container with the ingredients may be connected to the filter for example by way of piercing.

The bioreactor could, for example, be connected to a controlling and monitoring unit that controls a mixing operation and/or carries out pH measurements, conductivity measurements or other measurements or tests (release tests for media etc.).

The receiving container may be welded or fixedly connected directly to a sterile and/or virus filter or a combination of a sterile filter and a virus filter. The filter may be sterilized together with the receiving container. The receiving container may also be formed inter alia as a bag or bioreactor.

The receiving container may be connected releasably to a sterile and/or virus filter or a combination of a sterile filter and a virus filter.

The preparation container may be welded directly to a sterile and/or virus filter or a combination of a sterile filter and a virus filter.

The receiving container may include a mixing device of its own.

The preparation container and/or the receiving container may have at least one sensor for determining a parameter of the prepared substance mixture. In this respect, the pH value, the temperature, the conductivity or other parameters may be measured and, if appropriate, regulated by way of a controlling and monitoring unit. It is also possible to arrange a biochip, for example for determining sterility, in the preparation container and/or receiving container.

The invention also relates to a method for preparing mixtures of pharmaceutical or biopharmaceutical substances comprising the steps:
a) arranging a preparation container already made up with ingredients in a receptacle of a device,
b) feeding a fluid from a storage container into the preparation container via a feed line,
c) preparing the ingredients with the fluid into a substance mixture, and
d) removing the substance mixture from the preparation container into a receiving container via a discharge line.

The method step b) may be performed by a controlling and monitoring unit, where the feeding of the fluid may be based on predetermined or monitored parameters. The method step c) may be performed in a bag or bioreactor.

Adaptation of known methods for preparing mixtures of pharmaceutical or biopharmaceutical substances makes it possible, even under high-purity and/or sterile conditions, to prepare mixtures of pharmaceutical or biopharmaceutical substances relatively quickly, reliably and easily in small to medium amounts or volumes, in prescribable concentrations and media or components, that are made to suit the final consumer.

The feed line may also comprise a filter, for example a sterile filter. Similarly, the removal of the substance mixture may take place via such a filter. The filter may also be attached here directly to the receiving container (for example also be welded to it). Furthermore, the filter may include a mixing nozzle on the output side.

The already made up preparation container is closed off from its surroundings and is only connected to the feed line and the discharge line when it is received by the device, for example by piercing with a piercing spike.

Use of the already made up preparation container ensures the correct dosage of the ingredients.

The invention also relates to a method comprising the following steps:
a) arranging a preparation container in a receptacle of a device,
b) feeding ingredients from a plurality of storage containers into the preparation container,
c) feeding a fluid from a storage container into the preparation container via a feed line,
d) preparing the ingredients with the fluid into a substance mixture, and
e) removing the substance mixture from the preparation container into a receiving container via a discharge line for the preparation of mixtures of pharmaceutical or biopharmaceutical substances.

Feeding ingredients from a plurality of storage containers into the receiving container means that individual preparation with different components is possible or a variable composition of the substance mixture is possible while using the same preparation container.

The methods may be used for the preparation of medicaments that are individual to a patient, such as infusions or cytostatics or parenterals for example. Similarly, preparation of artificial blood, synthetic blood or blood substitute, such as hemoglobin-based blood substitutes or perfluorocarbons, for example, is possible.

The method may further include using a reading unit for reading out a coding of the preparation container after arranging the preparation container in the receptacle of a device and then calling up from a memory parameters that are necessary for carrying out the method and making the coding and those parameters available to a monitoring and controlling unit. The controlling and monitoring unit may selectively control at least one regulating valve to deliver an amount of fluid from a storage container to the preparation container based on the coding read by the reading unit and the parameters read from memory. Such parameters may include, but are not limited to, the pH value, the temperature, the conductivity or other parameters that may be measured. Thus automated preparation of the substance mixture is easy and reliable and at the same time makes an individual composition possible. Similarly, an identification can be implemented with the aid of electromagnetic waves (RFID) or other identification mechanisms.

Further details of the invention emerge from the following detailed description and the accompanying drawings, in which preferred embodiments of the invention are illustrated by way of example.

BRIEF DESCRIPTION OF THE DRAWINGS

FIG. 2 is a side view of a preparation container.

FIG. 3 is a view from below of the container of FIG. 2 from direction III.

DETAILED DESCRIPTION OF PREFERRED EMBODIMENTS

Figure 1:
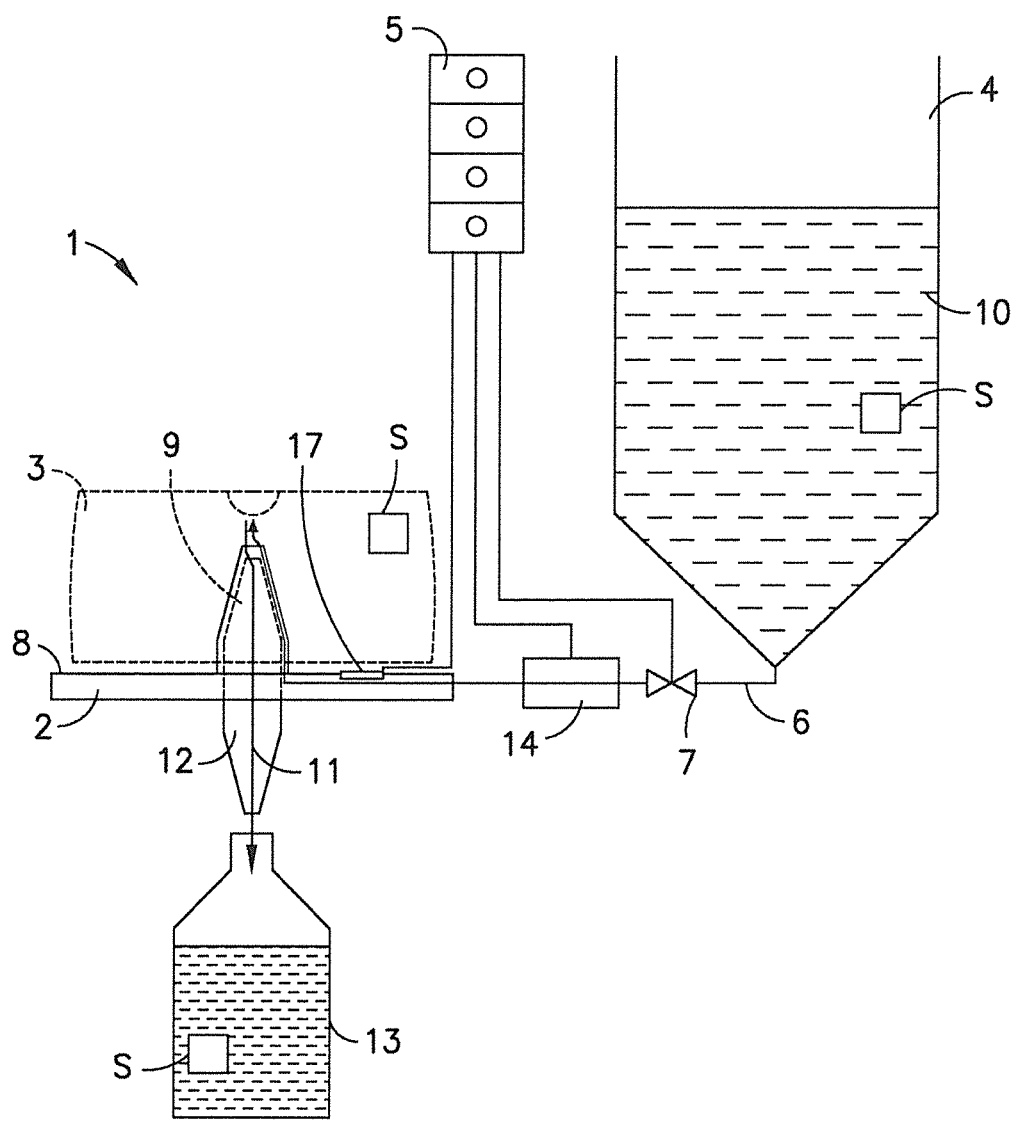
FIG. 1 is a schematic representation of a device for the preparation of mixtures of pharmaceutical or biopharmaceutical substances.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces. Herein, the phrase "coupled" is defined to mean directly connected to or indirectly connected with through one or more intermediate components. Such intermediate components may include both hardware and software based components.

It will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudocode, and the like represent various processes which may be substantially represented in computer readable media and so executed by a computer or processor, whether or not such computer or processor is explicitly shown. A device 1 substantially consists of a receptacle 2 for a preparation container 3, a storage container 4 and a controlling and monitoring unit 5. The functions of the controlling and monitoring unit 5 shown in the figures may be provided through the use of dedicated hardware as well as hardware capable of executing software in association with appropriate software. In one embodiment, the functions may be performed by at least one processor, such as a computer or an electronic data processor, digital signal processor or embedded micro-controller, in accordance with code, such as computer program code, software, and/or integrated circuits that are coded to perform such functions, unless indicated otherwise. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, read only memory (ROM) for storing software, random access memory (RAM), and nonvolatile storage. Other hardware, conventional and/or custom, may also be included in the controlling and monitoring unit 5, such as a memory, input/output interfaces, a wireless transceiver, analog-to-digital converters, etc.

Figure 9:
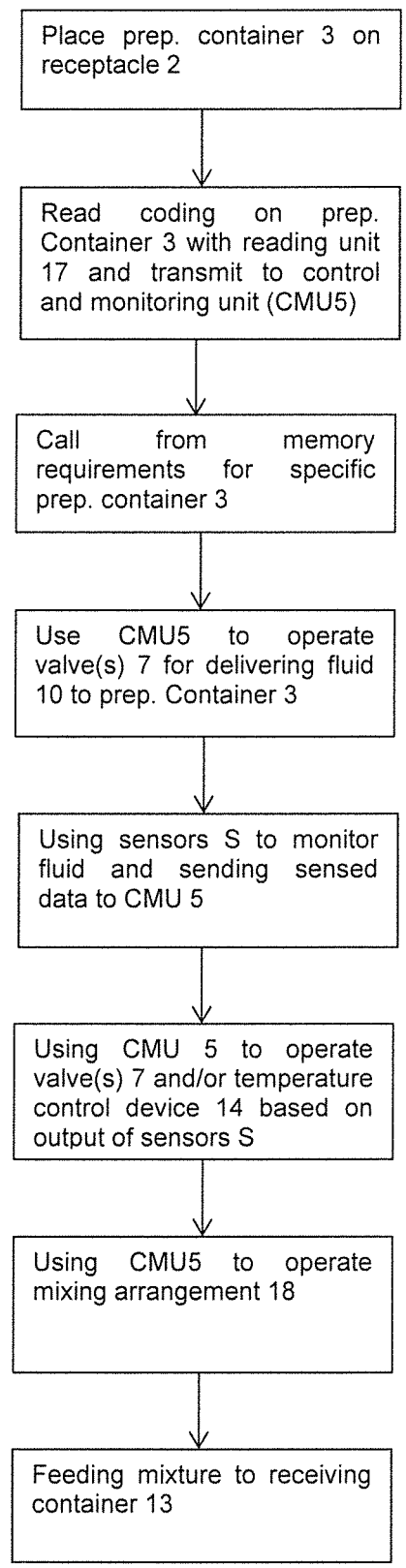
FIG. 9 is a flow chart illustrating one method of operation of the device of FIG. 1.

In the exemplary embodiment of FIG. 1, the receptacle 2 is connected to the storage container 4 by way of a feed line 6. A regulating valve 7 is arranged in the feed line 6 and is monitored and controlled by the controlling and monitoring unit 5. It is to be appreciated that the controlling and monitoring unit 5 controls the regulating valve 7 via an appropriate input/output interface, for example, a pneumatic actuator, electric actuator, etc. Suitable regulating valves 7 and control and monitoring units 5 are commercially available and include regulating valves sold by: Bronkhorst (e.g. Mini-Con-Flow™, Cori-Flow™, Liqui-Flow™, ES-Flow™, Liqui-View™, Cori-Flow Mini Cori-Flow Ex D™); Malema (e.g. BCV-910 Biopharma Control Valve™); Brooks Instruments and others The controlling and monitoring unit 5 may control the amount of a fluid via the input/output interface by opening and/or closing the regulating valve 7 or by modulating the regulating valve 7 for a particular flow rate. The receptacle 2 has an upper side 8 facing the preparation container 3, and a piercing spike 9 is provided on the upper side 8. After the placing of the preparation container 3 onto the receptacle 2, a fluid 10 located in the storage container 4 can be fed to the preparation container 3 via the piercing spike 9 and a prepared substance mixture 11 can be discharged into a receiving container 13 via a discharge line connected to the piercing spike 9. The fluid 10 to be fed to the preparation container 3 may be monitored by a sensor S coupled to the controlling and monitoring unit 5 via hardwire and/or wireless means and temperature-controlled in a temperature-controlling device 14 coupled to the controlling and monitoring unit 5. The preparation container 3 has an underside 15 facing the upper side 8 of the receptacle 2, and a coding 16, for example as a barcode, is provided on the upper side 8 of the receptacle 2. The coding 16 is read out by a reading unit 17 and fed to the controlling and monitoring unit 5. Although the reading unit 17 is shown wired to the controlling and monitoring unit 5, the reading unit 17 may communicate with the controlling and monitoring unit 5 via wireless means. The coding 16 is used by the controlling and monitoring unit 5 to call up from a memory, which is not represented any further, the parameters necessary for carrying out the method and to use them for carrying out the preparation method. For example, the controlling and monitoring unit 5 may selectively control at least one regulating valve 7 to deliver an amount of fluid from a storage container 4 to a preparation container 3 based on the parameters read from a memory, where the reading from the memory is based on the coding 16. Such parameters may include, but are not limited to, the pH value, the temperature, the conductivity, etc. An example of the above-described operation is illustrated by the flow chart in FIG. 9.

Figure 4:
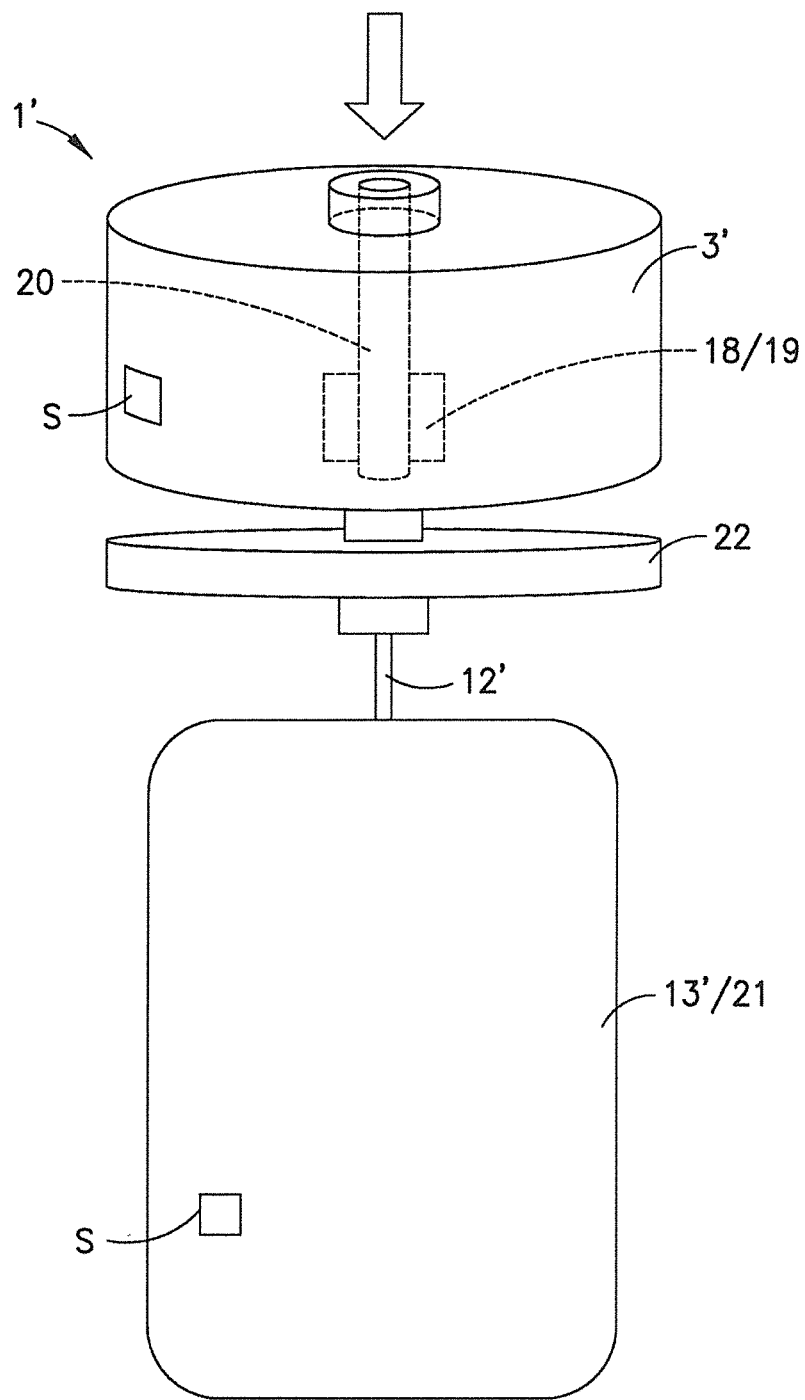
FIG. 4 is a schematic representation of a further device for the preparation of mixtures of pharmaceutical or biopharmaceutical substances with a sterile filter in the discharge line of the preparation container.

The exemplary embodiment of FIG. 4 shows a device 1' with a preparation container 3' that has a mixing arrangement 18 therein. The mixing arrangement 18 is illustrated as including an agitator 19 with an agitating shaft 20, but could, for example, have a magnetic agitator with a magnetic drive. Fluid or other ingredients, such as powder, can be fed via the mixing arrangement. A sterile filter 22 is arranged in the discharge line 12' upstream of the receiving container 13', which is formed as a disposable bag 21. The agitator may alternatively be attached in the bag or in the preparation container 3'. Sensors S may be arranged in the preparation container 3' and/or in the receiving container 13' to monitor conditions therein. It is to be appreciated that sensors S may provide the monitored parameters to the controlling and monitoring unit 5 via hardwire and/or wireless means. Such parameters may include, but are not limited to, the pH value, the temperature, the conductivity, etc. It is further to be appreciated the controlling and monitoring unit 5 may further control the at least one regulating valve 7 based on the monitored parameters to meet a predetermined setpoint for the parameters as determined by the read coding 16.

Consequently, a method can be carried out for example with the following steps:
a) arranging the preparation container 3' in the receptacle of the device 1',
b) monitored automatic feeding of ingredients and a fluid (for example water) 10 from corresponding storage containers into the preparation container 3',
c) preparing the ingredients with the fluid into a substance mixture, the substance mixture being thoroughly mixed by the mixing arrangement 18 or the agitator 19 thereof,
d) measuring prescribed parameters (for example conductivity, pH value and temperature) and approval
e) removing the substance mixture from the preparation container 3' via the sterile filter 22 (for example by breaking through a barrier) and via the discharge line 12' into the receiving container 13',
f) printing out a label and adhesive attachment to the preparation container, and
g) closing the preparation container 3' or the disposable bag 21 (for example by welding and detachment of the discharge line hose 12').

Figure 5:
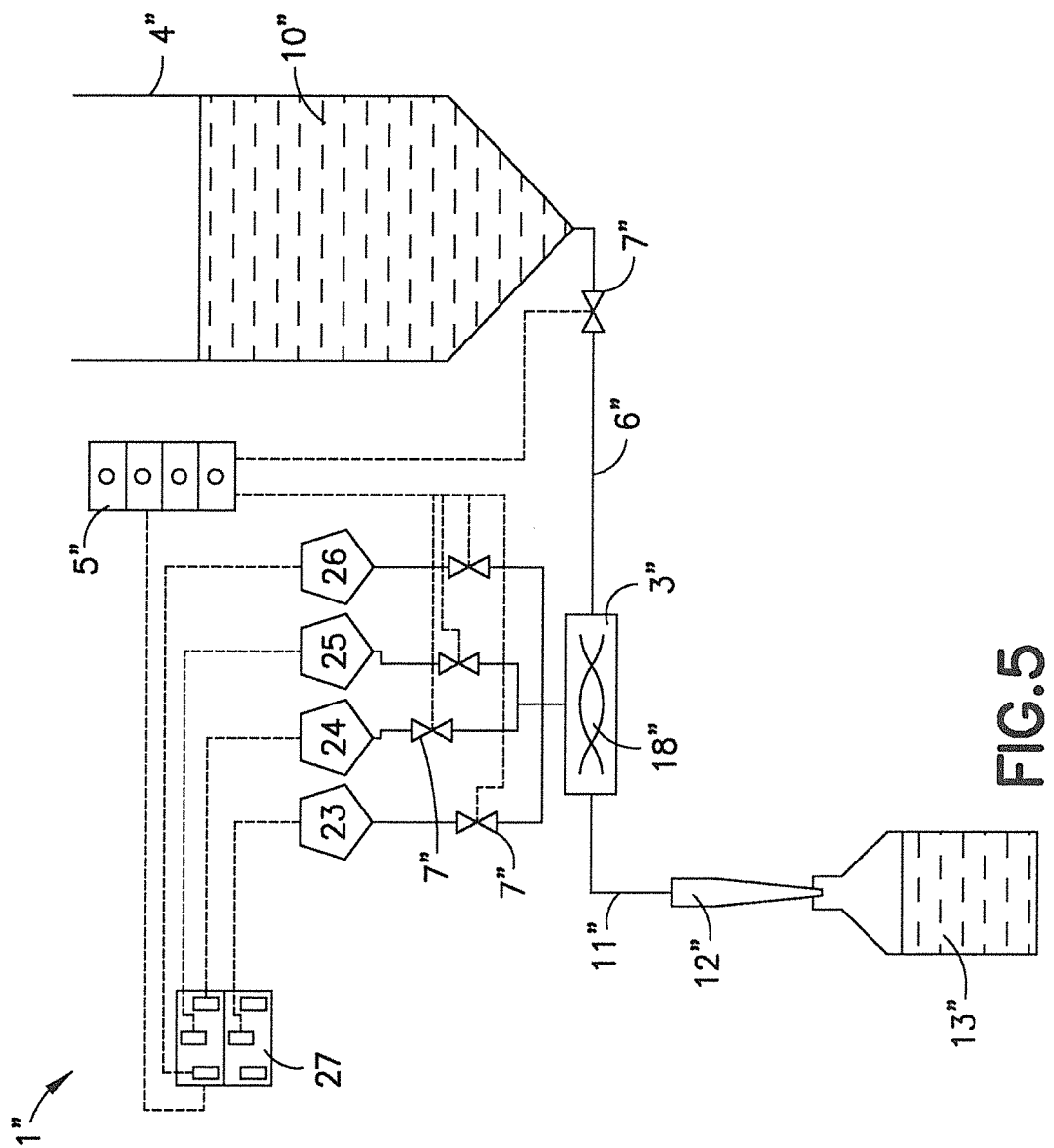
FIG. 5 is a further schematic representation of a device for the preparation of mixtures of pharmaceutical or biopharmaceutical substances with a plurality of storage containers.
Figure 5:
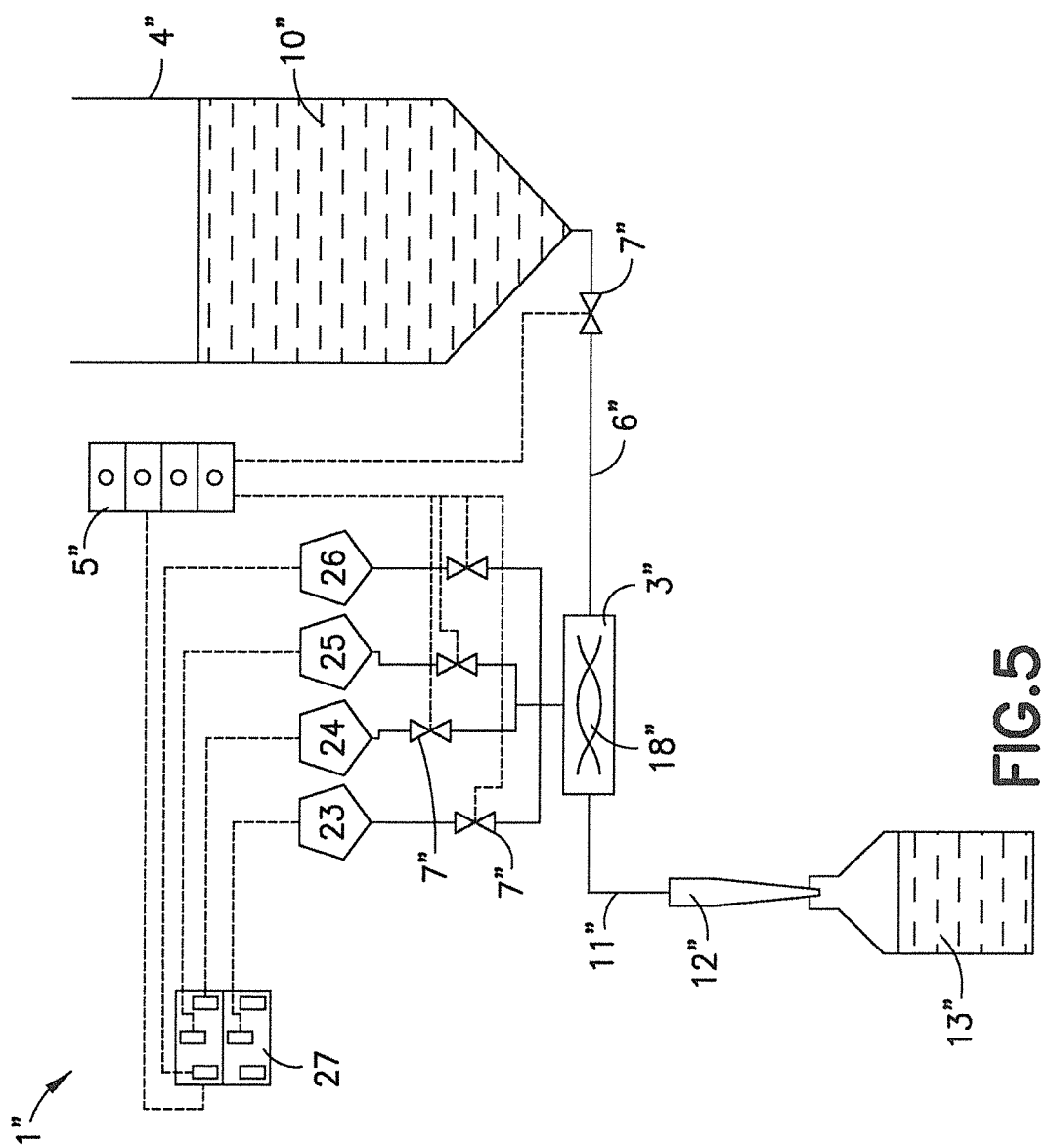

In the exemplary embodiment of FIG. 5, the device 1" has a preparation container 3" with a mixing arrangement 18". Arranged upstream of the preparation container 3" in the exemplary embodiment 4 are a plurality of storage containers 23, 24, 25, 26, via which the various media or ingredients can be fed by the controlling and monitoring unit 5" via assigned regulating valves 7". The fluid 10" from the storage container 4" is fed to the preparation container 3" likewise via a regulating valve 7". Correspondingly, the prepared substance mixture 1" is fed to a receiving container 13" via a discharge line 12". The storage containers 23, 24, 25, 26 can be manually selected both by way of the controlling and monitoring unit 5" and by way of a touchscreen 27. In one embodiment, the storage containers 23, 24, 25 26 may be automatically selected by the controlling and monitoring unit 5" based on the coding provided from the reader unit.

Figure 6:
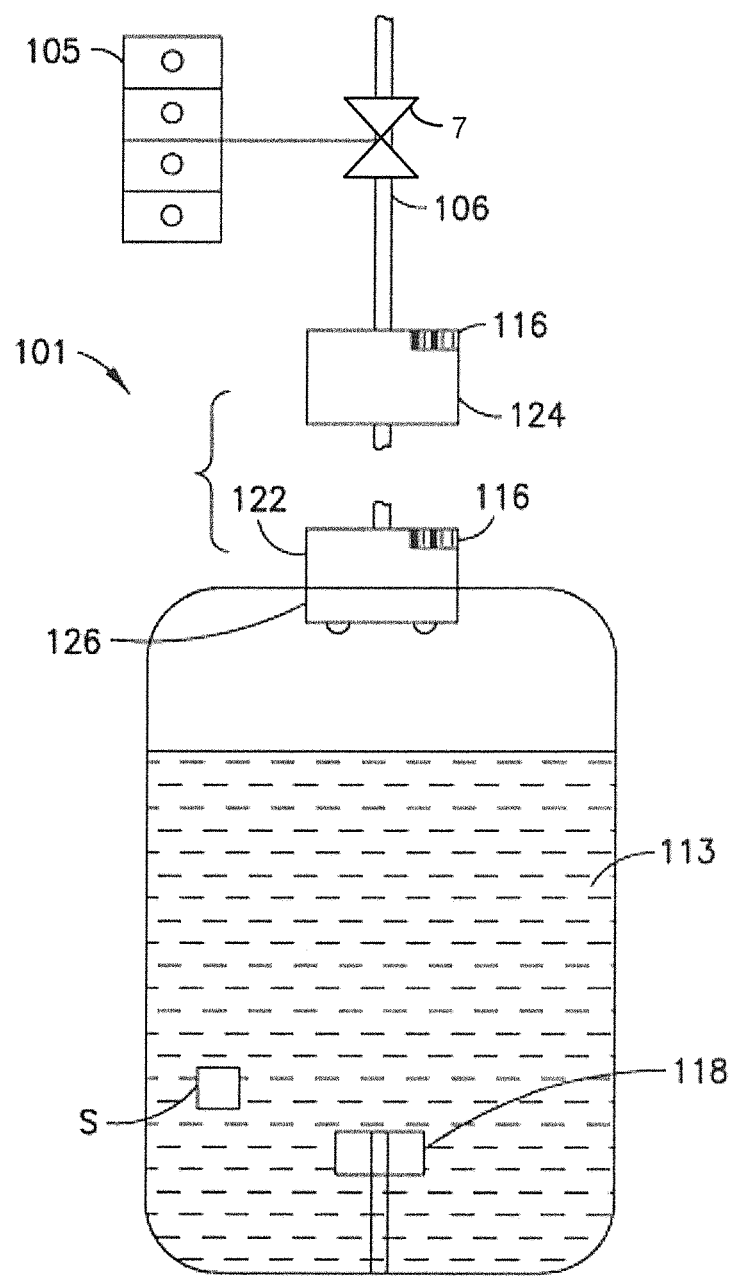
FIG. 6 is a schematic representation of a further device for the preparation of mixtures of pharmaceutical or biopharmaceutical substances with a sterile filter linked directly to receiving container.

FIG. 6 schematically illustrates a further embodiment of a device in accordance with the invention. The device 101 shown in FIG. 6 has a receiving container 113 in the form of a flexible disposable bag. A hose 106 extends from a storage container (not shown) similar to the storage container 4 shown in FIG. 1 and a preparation container similar to the preparation container 3 shown in FIG. 1. A controlling and monitoring unit 105 communicates with the hose 106 for controlling the flow of fluid through the hose 106, via a regulating valve 7, and toward the receiving container 113. A storage container 124 is incorporated into the hose 106 and may define a capsule with powder that is to be fed into the fluid directed to the receiving container 113. A sterile filter 122 is linked directly to the receiving container 113 for filtering fluid flowing through the hose 106 and into the receiving container 113. Coded indicia 116, such as barcodes, are provided on the storage container 124 and the sterile filter 122 and can be read by a code reader, as described with respect to the device 1 illustrated in FIG. 1. A mixing nozzle 126 is provided for for mixing and/or agitating the fluid mixture fed into the receiving container 113. Additionally, or alternatively, a mixing device 118, such as an agitator, may be provided within the receiving container 113. At least one sensor S is provided in the receiving container 113 for monitoring conditions therein. It is to be appreciated that the at least one sensor may provide the monitored conditions to the controlling and monitoring unit 5 via hardwire and/or wireless means. The device 101 function substantially as the other embodiments and has the advantages described above with respect to the other embodiments.

Figure 7:
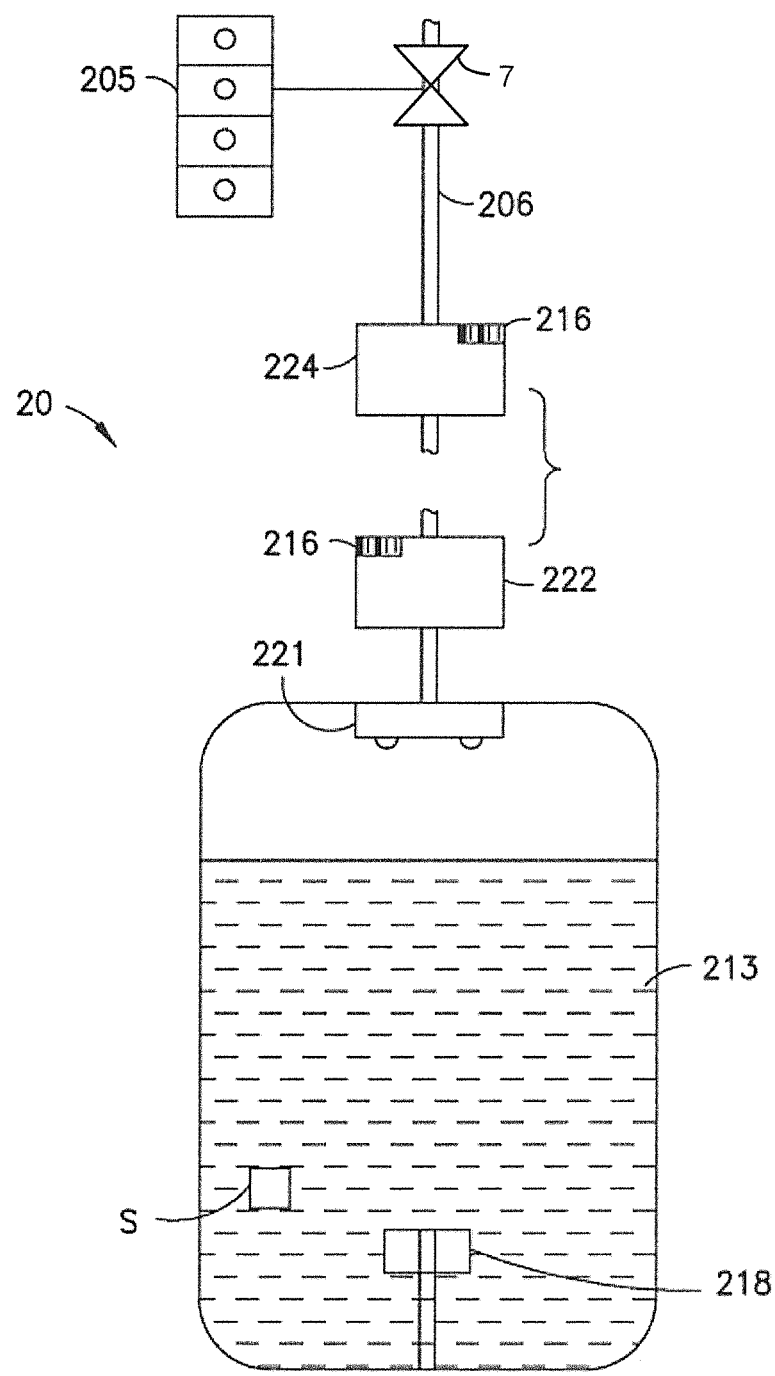
FIG. 7 is a schematic representation of a further device for the preparation of mixtures of pharmaceutical or biopharmaceutical substances with a sterile filter linked to receiving container via a tube.

FIG. 7 schematically illustrates a further embodiment of a device in accordance with the invention. The device 201 shown in FIG. 7 has a receiving container 213 in the form of a flexible disposable bag. A hose 206 extends from a storage container (not shown) similar to the storage container 4 shown in FIG. 1 and a preparation container similar to the preparation container 3 shown in FIG. 1. A controlling and monitoring unit 205 communicates with the hose 206 for controlling the flow of fluid through the hose 206, via a regulating valve 7, and toward the receiving container 213. A storage container 224 communicates with the hose 206 near the receiving container 213, and may define a capsule with powder that is to be fed into the fluid directed to the receiving container 213. A sterile filter 222 is linked to the receiving container 213 via a tube 223 for filtering fluid flowing into the receiving container 213. Coded indicia 216, such as barcodes, are provided on the container 224 and the sterile filter 222 and can be read by a code reader coupled to the controlling and monitoring unit 205, as described with respect to the device 1 illustrated in FIG. 1. A mixing nozzle 224 is provided for for mixing and/or agitating the fluid mixture fed into the receiving container 213. Additionally, or alternatively, a mixing device 218, such as an agitator, may be provided within the receiving container 213. At least one sensor S is provided in the receiving container 213 for monitoring conditions therein. It is to be appreciated that the at least one sensors may provide the monitored conditions to the controlling and monitoring unit 205 via hardwire and/or wireless means. The device 201 function substantially as the other embodiments and has the advantages described above with respect to the other embodiments.

Figure 8:
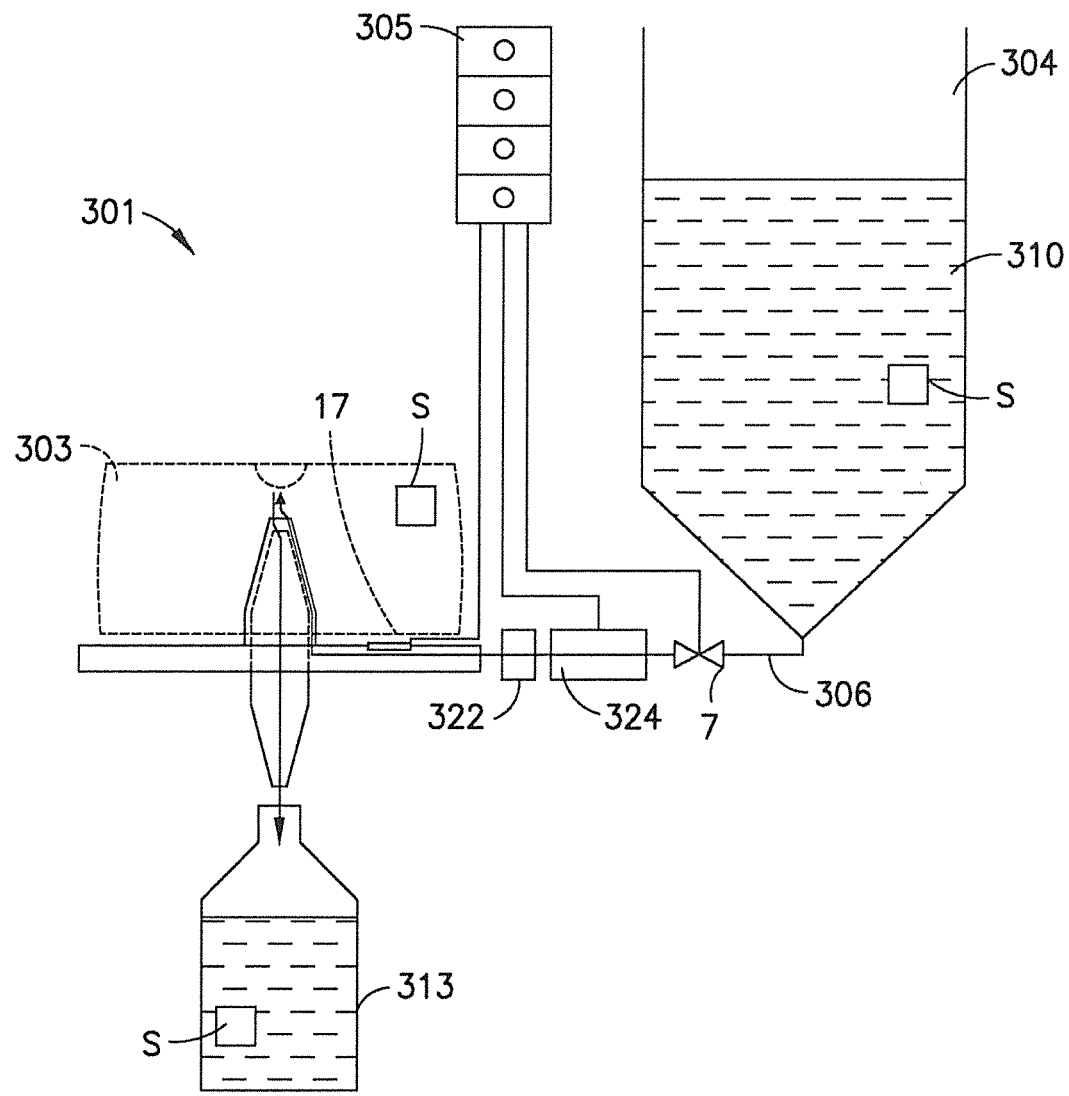
FIG. 8 is a schematic representation of a further device for the preparation of mixtures of pharmaceutical or biopharmaceutical substances with a sterile filter linked directly to the preparation container via a tube.

FIG. 8 schematically illustrates a further embodiment of a device 301. The device 301 is similar to the device 1 shown in FIG. 1. More particularly, the device 301 includes a preparation container 303 that is in communication with a storage container 304 via a feed line 306. A regulating valve 307 is arranged in a feed line 306 extending from the storage container 304 to the preparation container 303. A storage container 324 also is in communication with the feed line 306 and may contain a powder that is fed into the fluid 310 flowing through the feed line 306 and toward the preparation container 303. The device 301 differs from the preceding embodiments in that a sterile filter 322 is linked to the preparation container 303 via a tube 323. Coded indicia (e.g. barcodes) and readers are provided as in the other embodiments. This embodiment is particularly useful for larger units.

Of course, the embodiments discussed in the specific description and shown in the figures only represent illustrative exemplary embodiments of the present invention. In the light of the disclosure here, a person skilled in the art is offered a wide spectrum of possibilities for variation.

What is claimed is:

1. A device (1, 1', 1") for the preparation of mixtures of pharmaceutical or biopharmaceutical substances (11, 11"), comprising:
    a preparation container (3, 3', 3") with ingredients, the preparation container (3, 3', 3") carrying optically readable or RF scannable identifying information about the preparation container (3, 3', 3") and/or the ingredients therein;
    a receptacle (2) configured to receive the preparation container (3, 3', 3");
    a reading unit (17) adjacent the receptacle and configured to read the identifying information about the preparation container (3, 3', 3") and/or the ingredients therein;
    a storage container (4, 4") with a fluid (10, 10") that can be fed to the preparation container (3, 3', 3") via a feed line (6);
    at least one valve (7, 7") in the feed line (6) for controlling a flow of the fluid (10, 10") to the preparation container (3, 3', 3");
    a controlling and monitoring unit (5) communicating with at least the reading unit (17) and the valve (7, 7"), the controlling and monitoring unit (5) selectively opening and closing the valve (7, 7") for delivering an amount of the fluid (10, 10") from the storage container (4, 4") to the preparation container (3, 3' 3") based on the identifying information read by the reading unit (17);
    a receiving container (13, 13', 13") that communicates with the preparation container (3, 3', 3") via a discharge line (12, 12', 12"); and
    at least one sterile filter (22), or at least one virus filter or at least one combination of a sterile filter and a virus filter arranged between the storage container (4, 4") and the preparation container (3, 3', 3").

2. The device of claim 1, wherein the preparation container (3, 3', 3") has the at least one sterile filter (22) or the at least one virus filter or the at least one combination of a sterile filter and a virus filter.

3. The device of claim 1, wherein the preparation container (3, 3', 3") comprises a pad, on or in which the sterile filter or the virus filter or the combination of the sterile filter and the virus filter is arranged.

4. The device of claim 1, wherein the preparation container (3, 3', 3") and the receiving container (13, 13', 13") are welded to one another by way of a hose connection.

5. The device of claim 1, wherein at least one of the preparation container (3, 3', 3") and the receiving container (13, 13', 13") has at least one sensor for determining a parameter of the prepared substance mixture, the sensor communicating with the controlling and monitoring unit (5).

6. The device of claim 1, the at least one sterile filter (22), the at least one virus filter or the at least one combination of a sterile filter and a virus filter is connected fixedly to the receiving container (13, 13', 13").

7. A device (1, 1', 1") for the preparation of mixtures of pharmaceutical or biopharmaceutical substances (11, 11"), comprising:
    a preparation container (3, 3', 3") with ingredients, the preparation container (3, 3', 3") carrying optically readable or RF scannable identifying information about the preparation container (3, 3', 3") and/or the ingredients therein;
    a receptacle (2) configured to receive the preparation container (3, 3', 3");
    a reading unit (17) adjacent the receptacle and configured to read identifying information about the preparation container (3, 3', 3") and/or the ingredients therein;
    a storage container (4, 4") with a fluid (10, 10") that can be fed to the preparation container (3, 3', 3") via a feed line (6);
    at least one valve (7, 7") in the feed line (6) for controlling a flow of the fluid (10, 10") to the preparation container (3, 3', 3");
    a controlling and monitoring unit (5) communicating with at least the reading unit (17) and the valve (7, 7"), the controlling and monitoring unit (5) selectively opening and closing the valve (7, 7") for delivering an amount of the fluid (10, 10") from the storage container (4, 4") to the preparation container (3, 3' 3") based on the identifying information read by the reading unit (17);
    a receiving container (13, 13', 13") that communicates with the preparation container (3, 3', 3") via a discharge line (12, 12', 12"); and
    at least one sterile filter (22), or at least one virus filter or at least one combination of a sterile filter and a virus filter disposed in the feed line (6) between the valve (7, 7") and the preparation container (3, 3', 3").

8. A device (1, 1', 1") for the preparation of mixtures of pharmaceutical or biopharmaceutical substances (11, 11"), comprising:
    a preparation container (3, 3', 3") with ingredients, the preparation container (3, 3', 3") carrying optically readable or RF scannable identifying information about the preparation container (3, 3', 3") and/or the ingredients therein;
    a receptacle (2) configured to receive the preparation container (3, 3', 3");
    a reading unit (17) adjacent the receptacle and configured to read identifying information about the preparation container (3, 3', 3") and/or the ingredients therein;
    a storage container (4, 4") with a fluid (10, 10") that can be fed to the preparation container (3, 3', 3") via a feed line (6);
    at least one valve (7, 7") in the feed line (6) for controlling a flow of the fluid (10, 10") to the preparation container (3, 3', 3");
    a controlling and monitoring unit (5) communicating with at least the reading unit (17) and the valve (7, 7"), the controlling and monitoring unit (5) selectively opening and closing the valve (7, 7") for delivering an amount of the fluid (10, 10") from the storage container (4, 4") to the preparation container (3, 3' 3") based on the identifying information read by the reading unit (17);
    a receiving container that communicates with the preparation container (3, 3', 3") via a discharge line (12, 12', 12");
    at least one sterile filter (22), or at least one virus filter or at least one combination of a sterile filter and a virus filter arranged upstream or downstream of the preparation container (3, 3', 3"); and
    a temperature control unit (14) in the feed line (6) and communicating with the controlling and monitoring unit (5) for monitoring and controlling a temperature of a liquid being fed to the preparation container (3, 3', 3").

9. The device of claim 1, wherein the preparation container (3, 3', 3") has a readable code (16) thereon at a position to be read by the reading unit (17) for conveying to the controlling and monitoring unit (5) information about the preparation container (3, 3', 3") or the ingredients in the preparation container (3, 3', 3").

10. The device of claim 8, the at least one sterile filter (22), the at least one virus filter or the at least one combination of a sterile filter and a virus filter is disposed between the storage container (4, 4") and the preparation container (3, 3', 3").

* * * * *